("12") United States Patent  
Robinson et al.

(10) Patent No.: US 7,708,943 B1
(45) Date of Patent: May 4, 2010

(54) MICROFABRICATED FUEL HEATING VALUE MONITORING DEVICE

(75) Inventors: Alex L. Robinson, Albuquerque, NM (US); Ronald P. Manginell, Albuquerque, NM (US); Matthew W. Moorman, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 454 days.

(21) Appl. No.: 11/355,661

(22) Filed: Feb. 16, 2006

Related U.S. Application Data

(60) Provisional application No. 60/688,878, filed on Jun. 8, 2005.

(51) Int. Cl.
*G01N 25/20* (2006.01)
(52) U.S. Cl. .............................. 422/51; 422/89; 422/94
(58) Field of Classification Search ................. 436/153; 422/51, 83, 89, 90, 98, 93, 94
See application file for complete search history.

(56) References Cited

U.S. PATENT DOCUMENTS

| | | | |
|---|---|---|---|
| 6,068,684 | A | 5/2000 | Overton |
| 6,602,714 | B1 * | 8/2003 | Tagge et al. .................... 506/37 |
| 6,663,697 | B1 | 12/2003 | Kottenstette et al. |
| 6,666,907 | B1 | 12/2003 | Manginell et al. |
| 6,786,716 | B1 | 9/2004 | Gardner et al. |

OTHER PUBLICATIONS

C. Dücso, M. Ádáma, P. Fürjes, M. Hirschfelderb, S. Kulinyic, I. Bársony, "Explosion-proof monitoring of hydrocarbons by mechanically stabilised, integrable calorimetric microsensors", Sensors and Actuators B 95 (2003) 189-194.*
M. Moorman, "Microcombustor array and micro-flame ionization detector for hydrocarbon detection," Proc. Of SPIE, vol. 4981 (2003) 40-50.
M. Moorman, "Lower Heating Value Sensor for Fuel Monitoring," Submitted to IEEE Sensors (2005) SD-7933.
C. M. Matzke, "Microfabricated silicon gas chromatographic microchannels: fabrication and performance," SPIE vol. 3511, 262-268.
G. Lambertus, "Design, Fabrication, and Evaluation of Microfabricated Columns for Gas Chromatography," Anal. Chem, (2004), 76, 2629-2637.
P. N. Bartlett, "A Micromachined Calorimetric Gas Sensor: an Application of Electrodeposited Nanostructured Palladium for the Detection of Combustible Gases," Anal. Chem. (2003), 75, 126-132.
U.S. Appl. No. 11/067,107, filed Feb. 25, 2005.

* cited by examiner

*Primary Examiner*—Lyle A Alexander
*Assistant Examiner*—Dennis M White
(74) *Attorney, Agent, or Firm*—Kevin W. Bieg

(57) ABSTRACT

A microfabricated fuel heating value monitoring device comprises a microfabricated gas chromatography column in combination with a catalytic microcalorimeter. The microcalorimeter can comprise a reference thermal conductivity sensor to provide diagnostics and surety. Using microfabrication techniques, the device can be manufactured in production quantities at a low per-unit cost. The microfabricated fuel heating value monitoring device enables continuous calorimetric determination of the heating value of natural gas with a 1 minute analysis time and 1.5 minute cycle time using air as a carrier gas. This device has applications in remote natural gas mining stations, pipeline switching and metering stations, turbine generators, and other industrial user sites. For gas pipelines, the device can improve gas quality during transfer and blending, and provide accurate financial accounting. For industrial end users, the device can provide continuous feedback of physical gas properties to improve combustion efficiency during use.

14 Claims, 5 Drawing Sheets

MICROFABRICATED FUEL HEATING VALUE MONITORING DEVICE

CROSS-REFERENCE TO RELATED APPLICATION

This application claims the benefit of U.S. Provisional Application No. 60/688,878, filed Jun. 8, 2005, which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to the measurement of the heat generated by combustion of a fuel and, in particular, to a microfabricated fuel heating value monitoring device that can be used for real-time monitoring of the heating value of natural gas.

BACKGROUND OF THE INVENTION

The natural gas industry and large volume consumers are seeking inexpensive methods for real-time monitoring of natural gas (NG) constituents. Such real-time monitoring is especially needed for pipeline switching and metering stations, turbine generators, and other industrial user sites.

For pipelines, it is important to have information on the composition of NG in the main pipeline and of the blending in at every mixing location. When the fraction of heavier constituents is too high, it becomes unsuitable for certain end users. Heavier constituents may also condense where temperature and pressure drop, such as at meters, valves, and various locations in end-user facilities. Therefore, speciation is necessary to obtain the composition and hydrocarbon dew point of the NG.

It is also desirable by natural gas sellers and buyers to have immediate knowledge of the BTU value for equitable trade (a BTU, or British Thermal Unit, is the amount of heat required to raise the temperature of one pound of liquid water by 1° F. at its maximum density). Gas heating value and flow measurement errors on the order of a percent or less can have significant impacts to the industry in the areas of lost revenues and cash flow, since many pipeline networks possess gas transfer capacities that range from 0.5 to 1 billion cubic feet per day. As natural gas is sold by the BTU (i.e., the heating value), improved analysis will produce more equitable trade between buyers and sellers by reducing unaccounted for gas content. Because instrumentation for accurate natural gas analysis is expensive to purchase, operate and maintain, ubiquitous metering devices provide only volumetric measures of the quantity of natural gas consumed. However, final billing is determined a month or more later when information from lab analysis is used to convert the volumes to BTU heating values. This difference, known as unaccounted for (UFA) gas content, can be reduced by improved sample handling and analysis, producing more timely and accurate billing. A further complication arises during gas transfers between wholesale or commercial entities along the gas supply chain when both gas volume and heating value indices can be used in the transaction. Discrepancies between the two can result in billing errors or lost revenues. Therefore, a gas transfer system based solely on heating value and made possible by a low-cost approach would be beneficial to the natural gas industry.

Further, certain industrial users have a strong interest in knowing the composition of incoming natural gas. Industrial users will benefit through continuous feedback of physical gas properties during consumption, in particular with gas turbine engines used for power and electricity generation. For NG fueled turbines, efficiency of power generation is dependent on fuel properties and the temperature of the combustion cycle. Turbine controls are based on models that indirectly calculate peak combustor temperatures based on estimates of the fuel heating value. Inaccuracies as high as 40° C. limit the ability to operate at the optimum firing temperature. Controllers error on the side of safety to prevent part-life degradation from overfiring the turbines. Even a small increase in operational efficiency of natural gas-fueled power can save large amounts of natural gas per year and significantly reduce related nitrogen oxide emissions.

Finally, a low-cost monitoring device would enable distributed sensing of the natural gas infrastructure, providing greater pipeline security. Improved real-time information on the composition of gas throughout the system would allow early detection of deleterious events such as pipeline leakage or fouling.

The standard method for natural gas BTU analysis uses gas chromatography (GC) to speciate fuel flows, and then infers heating value from this speciation. See ASTM International 2003, "Standard Test Methods for Analysis of Natural Gas by Gas Chromatography," D1945-03. This method is highly accurate, but expensive in terms of equipment, maintenance, operation, and personnel. Samples are often collected into bottles for once-a-month lab analysis, resulting in billing accuracy delays of a month or longer. In addition, standard GCs and detectors require pressurized specialty gases, some of which are flammable. While slightly less expensive field-portable devices are becoming available, detector requirements have not changed. Automated on-line GCs are currently too expensive to widely distribute over the pipeline infrastructure for real-time analysis. Therefore, on-line GCs are only used at large custody transfer stations where accounting delays would become more costly. Under present conditions, the limited number of instrumentation locations within the gas pipeline network results in significant errors in mass balance and cost recovery that directly influence custody transfer operations. A number of research organizations are attempting to perfect inferential techniques using thermal conductivity or speed of sound measurements. Inorganic compounds such as carbon dioxide, carbon monoxide, and nitrogen confound these measurements, so their concentrations must be independently determined. So far, these techniques cannot determine nitrogen concentration without resorting to gas chromatography.

A pellistor is a type of calorimetric combustible gas sensor that detects a change in the temperature of a heated catalytic element when exposed to a mixture of combustible gas and air. Pellistors in the past have not been designed for speed. Most take several minutes to make accurate readings due to their large thermal masses and the thick diffusion-limiting layers of catalyst substrate on the surface of the sensing elements. Recently, much faster micropellistors, or microcalorimeters, have been developed for determining BTU heating values of natural gas and other fuel gas streams. See U.S. Pat. No. 6,786,716 to Gardner et al.; M. Moorman et al., "Microcombustor array and micro-flame ionization detector for hydrocarbon detection," *Proc. SPIE* 4981, 40 (2003); M. Moorman et al., "Lower Heating Value Sensor for Fuel Monitoring," submitted to *IEEE Sensors* (2005); and P. N. Bartlett and S. Guerin, "A Micromachined Calorimetric Gas Sensor: an Application of Electrodeposited Nanostructured Palladium for the Detection of Combustible Gases," *Anal. Chem.* 75, 126 (2003); which are incorporated herein by reference. The microcalorimeter typically comprises a thin catalyst layer deposited on a thin, resistively heated surface. The fuel, premixed with air, catalytically combusts on this surface. The heat of combustion is measured directly from a feedback circuit powering the sensor. This rapid and sensitive sensor provides a direct measurement of the BTU content of the fuel. When combined with a density measurement, the Wobbe Index can be determined, which is an important fuel property used to aid combustion control in systems such as gas turbines. This microcalorimeter provides stand-alone gas monitoring where low precision analysis (+/−5% BTU) is acceptable. However, while simple and inexpensive, this sensor alone does not provide direct information on constituents of the NG stream.

For many users, including gas transfer/mixing stations and electricity generating turbines, accuracy of 0.1% BTU is required. Further, for pipelines and turbines, speciation is necessary to obtain the NG composition and hydrocarbon dew point. Especially where large quantities of NG are consumed (medium-size or larger switching stations, gas-turbine electricity generators), all fuel properties need to be known. In these applications, widespread deployment of advanced monitoring devices is highly desirable. Further, for market acceptance, the monitoring device must be of low cost. Deployment of low-cost devices within the pipeline network would translate to increased revenues for the gas industry by virtue of more detailed information on the heating value of gas within the system at any given time. Industrial end users would benefit by running natural gas fueled turbines closer to design limits, safely maximizing power while maintaining pollution control.

SUMMARY OF THE INVENTION

The present invention is directed to a microfabricated fuel heating value monitoring device, comprising a microfabricated gas chromatography column, comprising a channel formed in a substrate, for separating the constituents of a fuel sample; and a catalytic microcalorimeter, comprising an active microhotplate having a catalyst deposited thereon, for combusting the separated constituents and measuring the heating value of the fuel sample. The fuel sample can be natural gas. The channel comprises an open or a packed channel. The microcalorimeter can further comprise a reference microhotplate to correct the active microhotplate signal for flow variations and thermal conductivity variations caused by the fuel constituents and carrier gas flowing over the microhotplates.

The microfabricated fuel heating value monitoring device has applications in the natural gas industry where more information about gas content is needed and where the cost of full GC instrumentation is currently prohibitively high. Potential monitoring sites include smaller pipeline switching stations, large industrial consumer locations, and remote natural gas production wells where sample tanks are filled in a time-integrated manner and typically analyzed on a monthly schedule.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
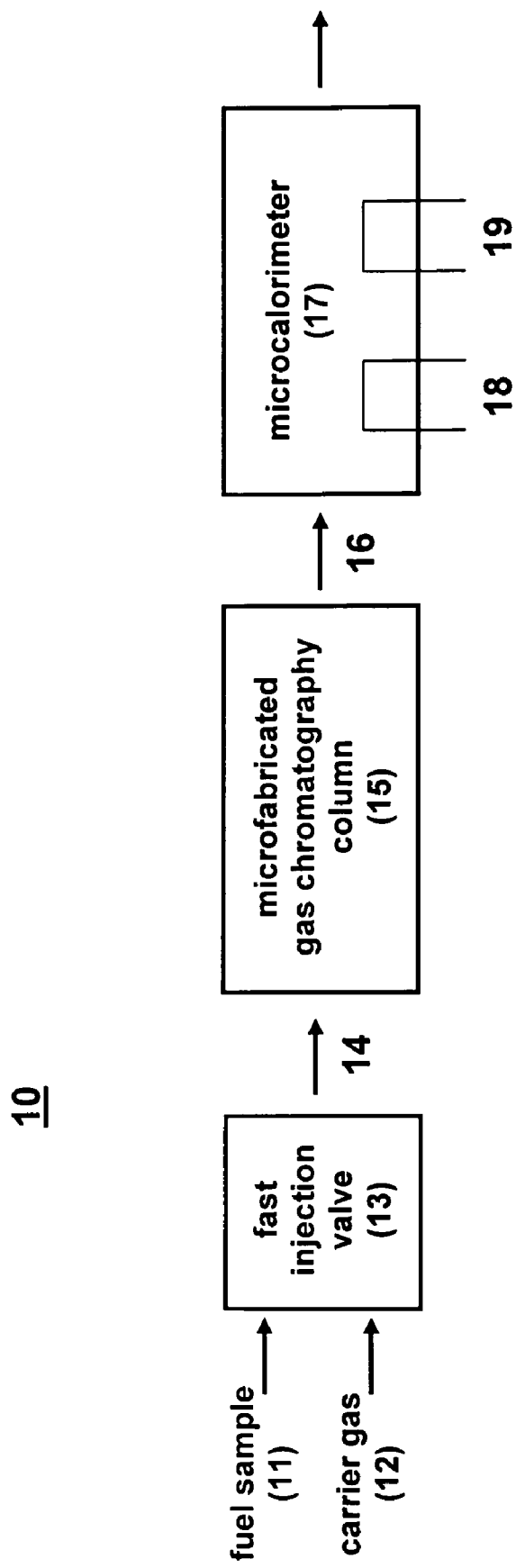
FIG. 1 shows a schematic illustration of the microfabricated fuel heating value monitoring device.

As shown in FIG. 1, the microfabricated fuel heating value monitoring device 10 of the present invention comprises a microfabricated GC column 15 in combination with a catalytic microcalorimeter 17. The GC column 15 and microcalorimeter 17 can be combined using either hybrid or monolithic methods. The microfabricated gas chromatography column comprises a channel formed in a substrate. To determine the heating value of a fuel sample 11, a small microliter volume 13 of the sample 11 is rapidly injected into the microfabricated GC column 15 using a fast injection valve 13. A carrier gas 12 pushes the fuel sample through the column 15, wherein constituents are separated as they traverse the length of the column. As the separated constituents 16 individually elute from the end of the column 15, they are quantitatively detected by the microcalorimeter 17. The microcalorimeter 17 comprises an active microhotplate 19, having a catalyst formed thereon, to record the combustion of the separated constituents. The microcalorimeter 17 can further comprise a reference microhotplate 18 to serve as a thermal conductivity detector and to correct the active microhotplate signal for flow variations and thermal conductivity variations caused by the fuel constituents and carrier gas flowing over the microhotplates. One or more additional columns and calorimeters can be used to rapidly analyze both light and heavy constituents simultaneously. Microfabrication techniques allow the device to be manufactured in production quantities at a low per unit cost.

Natural gas comprises primarily methane gas, along with carbon dioxide, nitrogen, and hydrocarbons up to C9. It is almost entirely the hydrocarbon content that determines the BTU content, and thus the heating value, of each unit of natural gas (e.g., hydrogen and hydrogen sulfide also contribute to heating value). Higher heating value accuracy is achieved with the present invention through separation of the fuel sample constituents using the GC column before sensing with the microcalorimeter. The microcalorimeter measures only combustible constituents which contribute to the fuel heating value. Characterization of the individual constituents of a natural gas sample enables precise determination of the BTU content of the fuel sample. Speciation and/or accuracy of +/−0.1% BTU can be achieved using this device. Further, analysis duration is reduced with little or no loss of performance by scaling down analytical component size, volume, and internal dead volume. Continuous calorimetric determination with a 1 minute analysis time and 1.5 minute cycle time can be achieved using air as a carrier gas and oxidant for the catalytic sensor.

The constituents in the fuel sample are first separated in a gas chromatograph. Gas chromatography relies upon the chemical equilibria of the constituents between a mobile phase and a stationary phase in a GC column to bring about a temporal separation of the constituents in a gas mixture into a series of elution bands. Traditional methods of GC rely on an open capillary tube with a stationary phase coating the inner wall of the tube to generate chemical separations. In addition, GC columns can be packed with porous polymer beads, adsorption beads, or supports with other stationary phases to achieve chemical separations.

Portable, handheld microanalytical systems, which have been termed "chemical laboratories on a chip," are being developed based on gas chromatography. Open, packed, and porous-layer open-tubular channels have been used with current GC-based microanalytical systems. Such GC columns can be fabricated in a variety of materials using a variety of microfabrication techniques. For example, the column substrate can comprise silicon, nickel, glass, aluminum, stainless steel, polymer, or other material suitable for chromatography columns. Etched silicon channels are commonly used for microfabricated GC columns. Anisotropic wet etching or reactive ion etching can be used to form high-aspect-ratio rectangular channels with precisely controlled channel depth and width in a silicon wafer. Typically, rectangular channels are about 10 to 80 microns wide and about 200 to 400 microns deep etched in the surface of the silicon wafer. For dense packing, the channels typically have a spiral or serpentine pattern in a die that is approximately one square centimeter in area. The inside wall surfaces of the channel can be coated with a stationary phase material to enhance the separation of the chemical constituents of interest in a gas sample. For example, the stationary phase material can be a polymer having a specific chemical group with the proper physicochemical interaction to cause separation of the constituents. Instead of using a stationary phase material to coat the surfaces of the channel, the channel can alternatively be filled with various packing materials (e.g., coated solid beads, high surface area uncoated beads, or polymer beads). Finally, the microfabricated column can be heated by a thin-film resistance heater deposited on the unetched side of the substrate. Overall column length is typically about 1 meter for open channels and as short as 5 centimeters for packed channels. See C. M. Matzke et al., "Microfabricated Silicon Gas Chromatographic MicroChannels: Fabrication and Performance," *Proceedings of SPIE, Micromachining and Microfabrication Process Technology IV,* 3511, 262 (1998); G. Lambertus et al., "Design, Fabrication, and Evaluation of Microfabricated Columns for Gas Chromatography," *Anal. Chem.* 76, 2629 (2004); U.S. Pat. No. 6,068,684 to Overton; U.S. Pat. No. 6,663,697 to Kottenstette et al.; U.S. Pat. No. 6,666,907 to Manginell et al.; and U.S. patent application Ser. No. 11/067, 107 to Lewis et al., which are incorporated herein by reference.

Wall-coated open channel and packed microfabricated GC columns have relative advantages and disadvantages. In general, which type of column to use ultimately depends upon the nature of the compounds being separated and the operating conditions of pressure and temperature that constrain the analysis or equipment. To date, fast-GC separations based on microfabricated GC columns have used almost exclusively low volatility samples in open channel columns. These microfabricated open-channel columns are designed for faster separations, but with less efficiency. Therefore, these open-channel columns, typically coated with polydimethylsiloxane (PDMS), are not optimized for the separation of high volatility, light hydrocarbons. However, microfabricated porous-layer open-channel columns, which are a cross between wall-coated open-channel and packed columns, can achieve reasonable separations for higher volatility samples.

Figure 2:
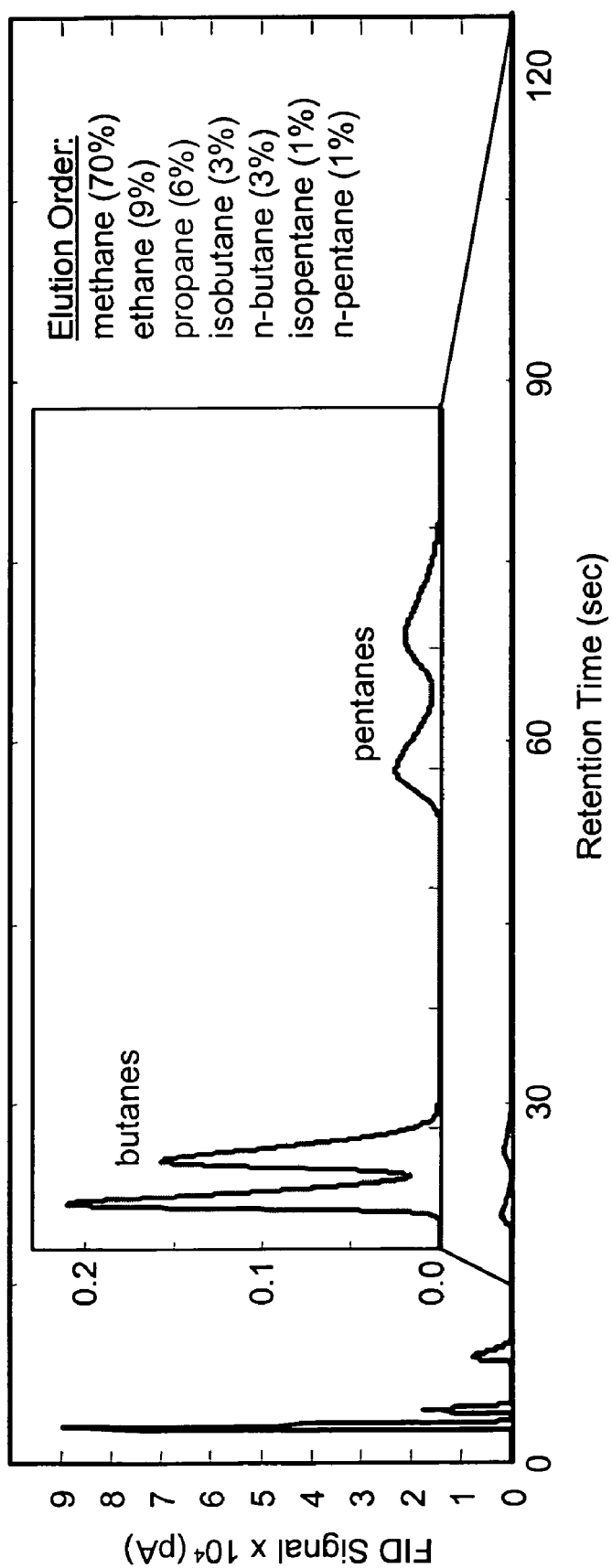
FIG. 2 shows a chromatogram of the separation of 5 μL natural gas using 20-cm long microGC column packed with HayeSep B, 100° C., 10 p.s.i.

Packed microfabricated GC columns tend to provide better separations for light hydrocarbons. In FIG. 2 is shown a chromatogram of the separation of a 5-µL NG sample obtained using a microfabricated GC column having a 20-cm long rectangular channel formed in a silicon wafer, with cross-sectional dimensions of 300-µm width×300-µm depth and packed with HayeSep B porous polymer beads (Supelco, Bellefonte, Pa., a division of Sigma-Aldrich Corp.). The separated NG constituents were measured with a flame ionization detector (FID). This packed column separated C1-C3 hydrocarbons in under 15 seconds at 100° C. with 10 p.s.i air carrier gas. Complete elution of all compounds occurred in just over 2 minutes. The C4 and C5 groups are well separated from each other, but there is overlap of the isomers. The BTU values of conformational isomers are similar to within 0.2%. Assuming the sample contained 6% of just one butane isomer, using an unweighted average of the BTU values produces a maximum systematic error of 0.02% in the BTU calculation. For many industrial applications, the emphasis is on faster analysis times and the elucidation of isomers is not necessary. Therefore, analysis of C1-C5 with partial separation of isomers can be performed in less than 70 seconds before degradation of the C1/C2 peaks occurs with this column. A 25-cm long column would baseline separate the isomers, but at a cost of 25% longer analysis time and the need for a higher driving pressure.

Figure 3:
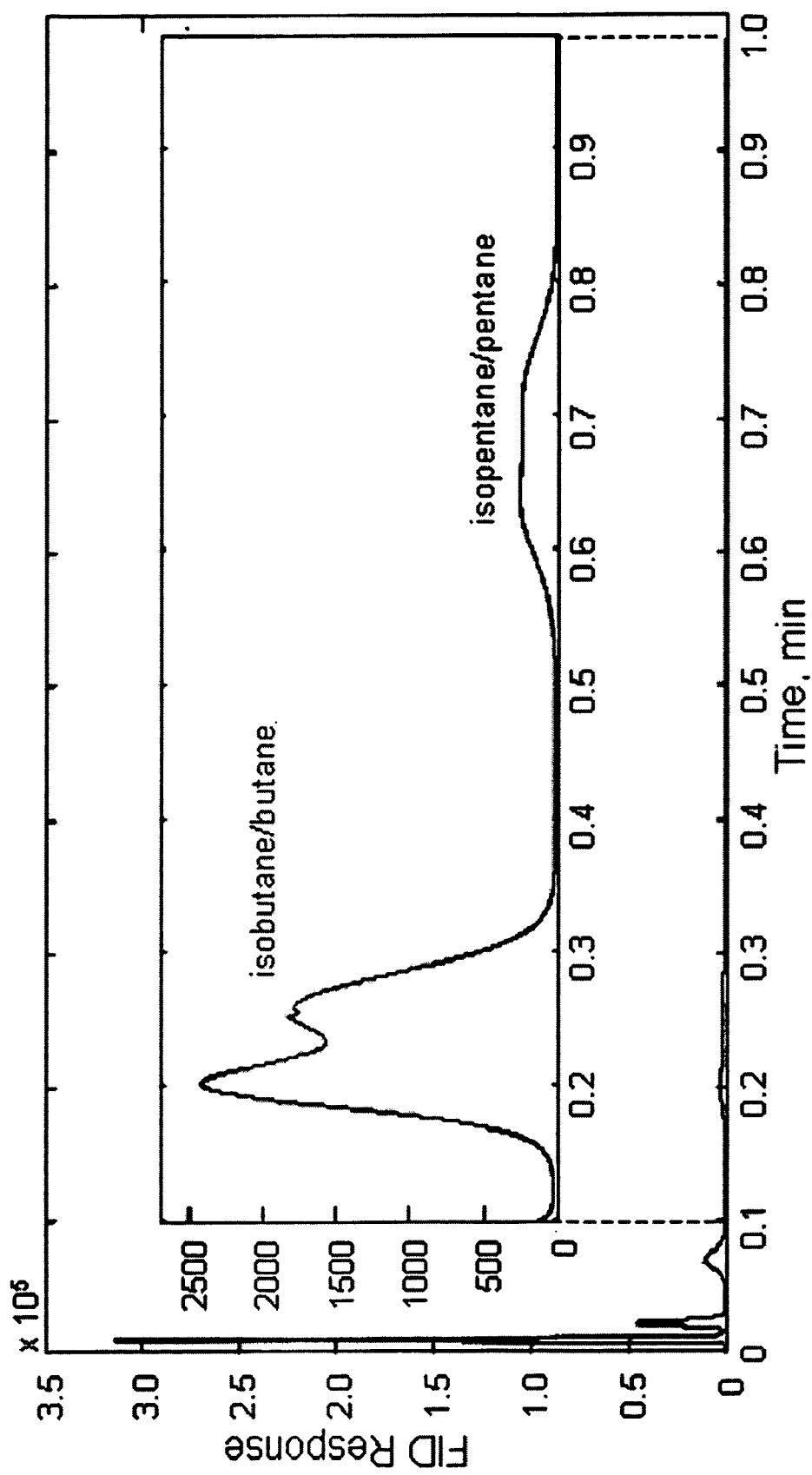
FIG. 3 shows a chromatogram of the separation of 5 μL natural gas injection using 15-cm microGC column packed with HayeSep D, 20 p.s.i. air carrier, temperature ramp from 80 to 120° C. at 40° C./min. Inset is magnified 100×.

In FIG. 3 is shown a chromatogram of the same 5 µL NG sample separated with a 15-cm column having similar channel dimensions and packed with HayeSep D polymer beads. The column temperature was ramped from 80 to 120° C. at 40° C./min. Thermal ramping of the low-mass silicon column speeds the run time considerably while maintaining excellent resolution of the first eluting compounds. This column separated all of the constituents of the NG sample by carbon number, but with little isomer separation, in less than one minute. Partial separation of the isomers here produces a maximum 0.003% error in the BTU (heating) value for each one percent of C4+C5 hydrocarbons in the mixture. This accuracy is well within industry requirements and sufficient for most combustion applications.

Figure 4:
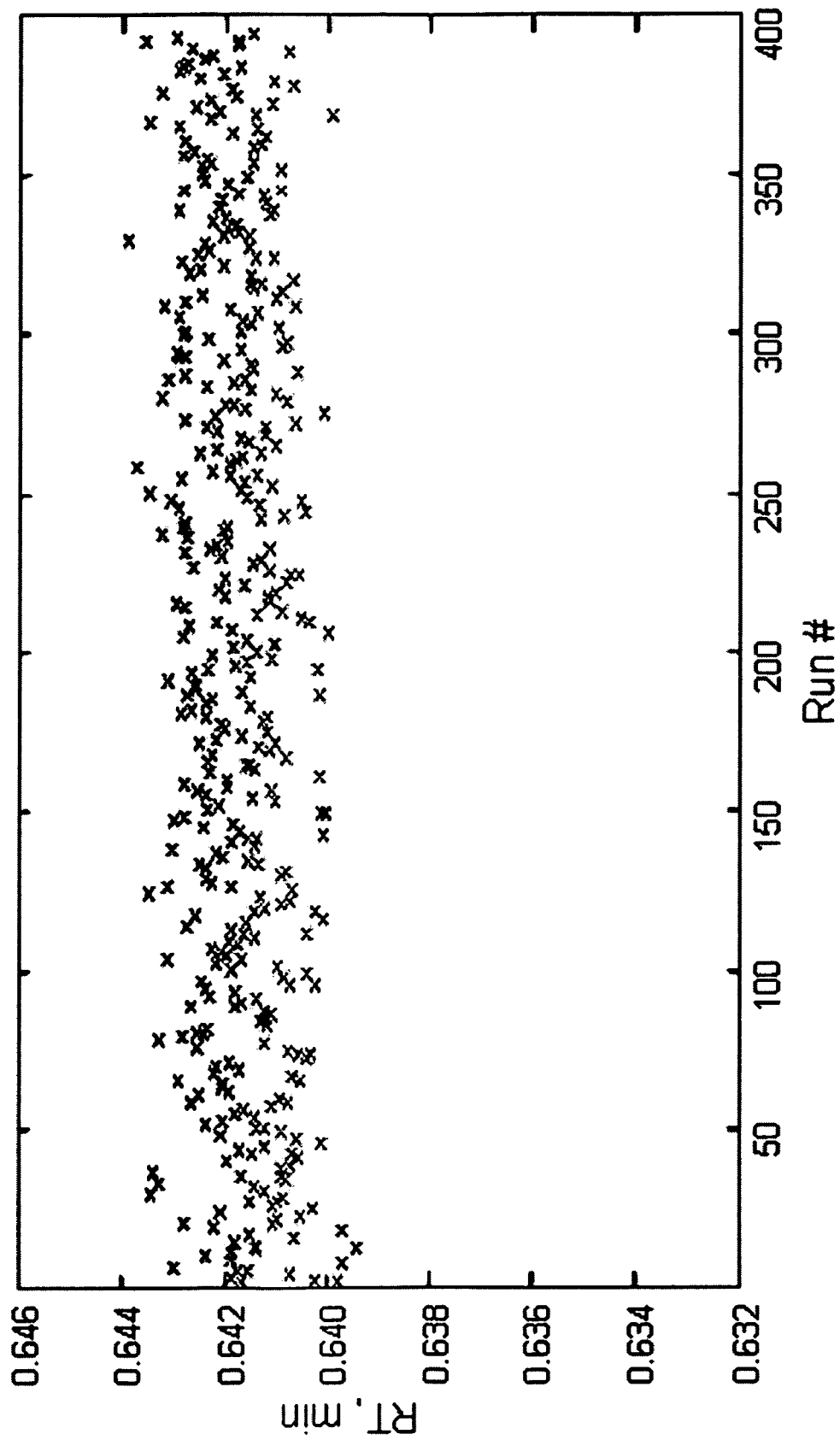
FIG. 4 shows a graph of the retention time stability of isopentane is 0.05 seconds absolute standard deviation, or 0.1% drift on 39 second retention time.

Since the microcalorimeter uses air as the oxidant, any GC column material chosen for use with the microcalorimeter is preferably compatible with air as a carrier gas up to the maximum separation temperature. HayeSep D does not decompose until above 300° C. in air, as demonstrated using thermogravimetric analysis. In FIG. 4 is shown a graph of the retention time (RT) stability of isopentane using this column packed with HayeSep D. This packing showed no performance degradation, with thermal cycling of the GC column from 80 to 120° C., and excellent reproducibility of all peak positions over the course of the runs. The column stability has a 0.05 seconds absolute standard deviation, or 0.1% drift on 39 second retention time over the course of 400 chromatography runs.

The separated constituents are sensed by the microcalorimeter. The microcalorimeter comprises a microhotplate and a catalyst deposited thereon for rapid combustion on the microscale. The microcalorimeter responds to the presence of a hydrocarbon as it catalytically combusts on or near the heated active surface of the microhotplate. The microhotplate has very low heat capacity and thermal conductivity that mitigate large heat losses arising from large surface-to-volume ratios typical of the microdomain. The heated catalyst enables flame ignition and stabilization, permits combustion with lean fuel/air mixtures, extends a hydrocarbon's limits of flammability, and lowers the combustion temperature. The reduced operating temperatures enable a longer microcalorimeter lifetime, which is especially important for portable microsystems applications. The very low thermal mass of the microcalorimeter allows a response fast enough to capture chromatography peaks. Further, the microcalorimeter provides robustness, resilience to high temperature and thermal shock, catalyst adhesion, and overall device survivability for unattended operation. See U.S. Pat. No. 6,786,716 to Gardner et al.; and M. Moorman et al., "Microcombustor array and micro-flame ionization detector for hydrocarbon detection," Proc. SPIE 4981, 40 (2003); which are incorporated herein by reference.

The microhotplate can be formed in a variety of materials, such as silicon, polysilicon, silicon carbide, silicon nitride, metal, or other material suitable for catalyst support. For example, the microhotplate can comprise a 1-μm thick silicon nitride membrane suspended from a frame of silicon. The fabrication process starts with a silicon wafer with a thin layer of low-stress silicon nitride. A thin-film pattern of electrically resistive metal is deposited on the membrane over the future etch pit. This later serves as a heater to elevate the membrane temperature during catalytic operation. The heater typically comprises a 10-nm tantalum adhesion layer under approximately 170-nm platinum layer. The temperature coefficient of resistance (TCR) of the platinum can be used to dynamically monitor membrane temperature during operation. Alternating layers of plasma enhanced chemical vapor deposition (PECVD) silicon nitride and silicon dioxide are then deposited over the wiring to provide a diffusive barrier to oxygen and moisture. These layers can be approximately 50-100 nm thick, with the total stack thickness measuring about 300 nm. This dielectric stack also improves adhesion of the catalyst layer. Photolithographic patterning coupled with deep reactive ion etching or potassium hydroxide etching are then used to selectively remove silicon in a pit underneath the heater wires, releasing the silicon nitride membrane. The membrane then serves as support for a high surface area platinum catalyst layer.

Subsequent to microhotplate fabrication, a catalyst layer is deposited directly on the microhotplate membrane. The particular choice of catalyst and operating temperature is dependent upon the fuel to be analyzed. The catalyst can be, for example, a noble metal, noble metals with additives, semi-conducting oxides, or hexaaluminate materials. The catalyst can be supported in high-temperature-stable, high-surface-area materials, such as alumina, hexaaluminates, zirconia, ceria, titania, or hydrous metal oxides (e.g., hydrous titanium oxide (HTO), silica-doped hydrous titanium oxide (HTO:Si), and silica-doped hydrous zirconium oxide (HZO:Si)). The range of catalyst loading can preferably be about 0.05 to 10 percent by weight. These supported catalysts have good stability and reactivity and help to mitigate against reliability problems and failure modes. Alumina-supported catalysts comprising noble metals, such as Pt or Pd, supported in an alumina matrix are commonly used.

The catalyst used to test the microcalorimeter comprised 10% platinum particles (w/w), with gamma alumina particles forming the balance. A slurry consisting of these particles and pH balanced water was created to facilitate deposition. The Pt-loaded alumina slurry was used as the catalyst for the active microhotplate. A similar slurry of alumina was also prepared to deposit on the reference microhotplate. The slurries were deposited with a nebulizer. The nebulizer sprays the slurries through a shadow mask onto the microhotplates heated to 160° C. This quickly evaporates the liquid, resulting in well-defined and robust catalyst spots. After deposition, the coated microhotplates were placed in a vacuum oven for 12 hours at 60° C. to make certain all liquid was removed before microcalorimeter operation.

The reference microhotplate serves as a thermal conductivity detector and corrects the active microhotplate signal for flow variations and thermal conductivity variations caused by the gas and air flowing over the heated microhotplates. The active microhotplate possesses the catalyst spot, and hence records the hydrocarbon combustion. Fixture heating, usually to 40° C., was used to minimize signal drift caused by environmental fluctuations. Water condensation from combustion was carried away by the gas streams before condensation could occur.

During operation, both microhotplates were connected to a temperature-control circuit. The circuit maintained the microhotplates at a user-defined temperature, usually 400-500° C., by monitoring the resistance of the membrane heater and controlling the input power in an active feedback loop. External heating from hydrocarbon combustion, or cooling from gas flow, tries to drive the temperature up or down, thus modifying the effective resistance of the membrane heater. This causes the circuit power to change to maintain the desired resistance. This feedback mechanism maintains constant microhotplate resistance, and hence constant temperature. Excursions in applied power from the zero-hydrocarbon baseline power constitute the signal of the microcalorimeter. Power is recorded as the product of applied voltage and current.

Experiments were conducted with the microcalorimeter to optimize combustion behavior during chromatography. This involved optimizing combustion efficiency by optimizing flow rate, dead volume over the microhotplates, and microhotplate temperature during static hydrocarbon exposures. An average surface temperature of 480° C. was determined to maximize combustion while providing long lifetime. Flow rate was optimized in the range of 30 to 40 mL/min. Rapid combustion responses were measured on the active catalyst microhotplate, along with negative responses on the reference microhotplate.

Figure 5:
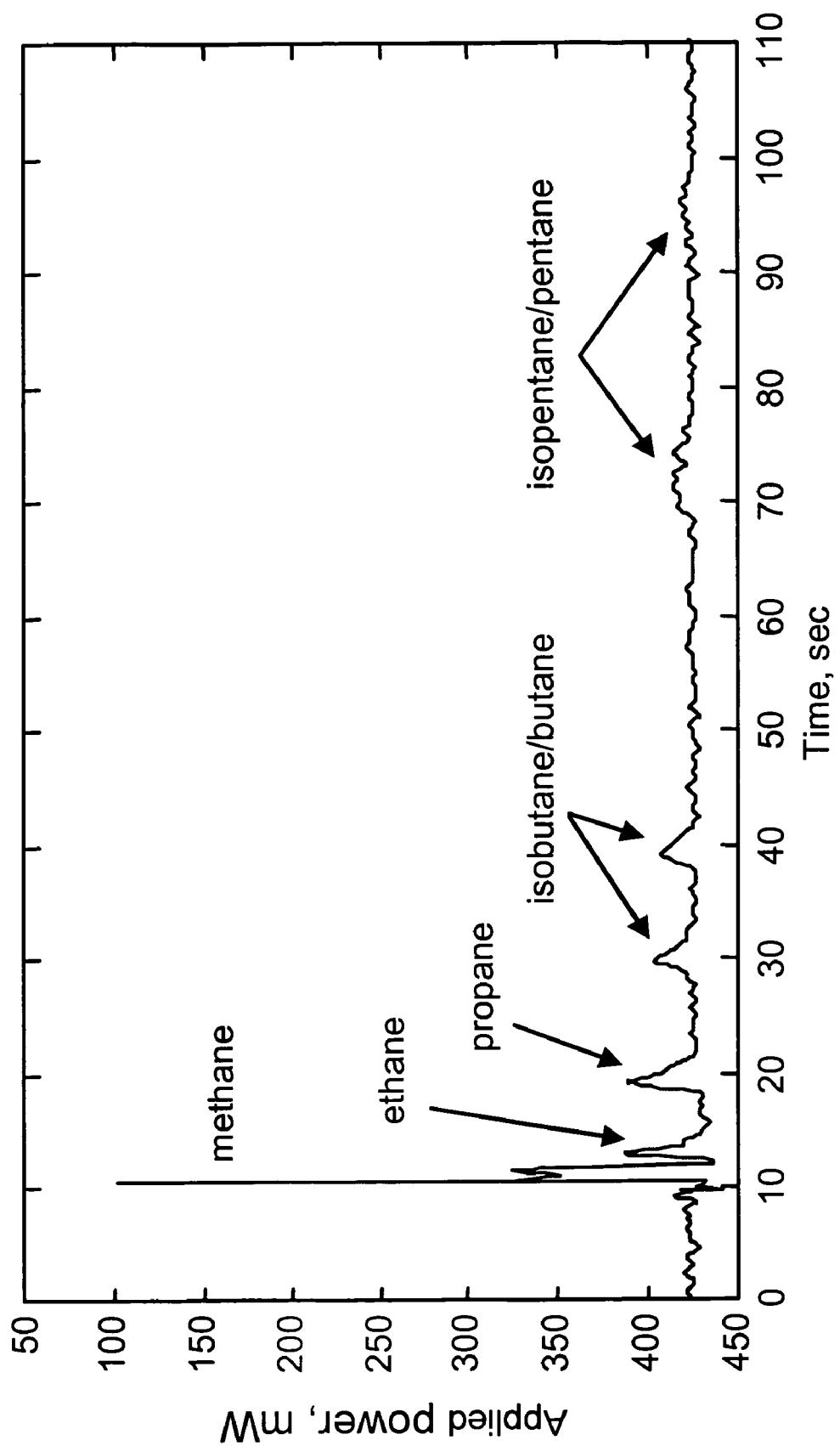
FIG. 5 shows the sensing of natural gas compounds, separated using a commercial column, using a microcalorimeter.

The microcalorimeter was connected to a commercial chromatography column (Agilent Technologies; 15 m, 0.53 mm I.D., DB-1, 1.25 μm phase) at room temperature. A commercial injection valve provided 5 μL injections of NG, and a lecture bottle delivered pressurized air as a carrier gas/oxidant. In FIG. 5 is shown the microcalorimeter signal from combustion of natural gas compounds separated using the commercial column. The ordinate axis is given in units of power (milliwatts) applied to the microhotplate heater to maintain a fixed 400° C. temperature. As hydrocarbons combust on the catalytic surface, less power is required to maintain this temperature. The scale has been inverted to clarity to appear as a typical chromatogram. This signal was collected at a sub-optimal sampling rate of 10 Hertz. Sensitivity could be greatly improved with Improvements in the electronics and in the dead-volume of the sensor fixture.

The present invention has been described as microfabricated fuel heating value monitoring device. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A microfabricated fuel heating value monitoring device, comprising:

a microfabricated gas chromatography column, comprising a channel formed in a substrate, for separating the constituents of a fuel sample; and a catalytic microcalorimeter, disposed downstream of the gas chromatography column, comprising an active microhotplate having a catalyst deposited thereon, a resistive heating element disposed on a side of the microhotplate, a combustion chamber on the catalyst-side of the microhotplate for combustion of the separated constituents thereon, and an electrical control circuit for powering the resistive heating element and monitoring the chance in the electrical characteristics of the resistive heating element in response to the heat liberated from the combustion of the separated constituents and measuring the heating value of the fuel sample.

2. The device of claim 1, wherein the fuel sample comprises natural gas.

3. The device of claim 1, wherein the gas chromatography column substrate comprises silicon, nickel, glass, aluminum, stainless steel, or polymer.

4. The device of claim 1, wherein the channel comprises an open channel.

5. The device of claim 1, wherein the channel comprises a packed channel.

6. The device of claim 1, wherein the channel comprises a porous-layer open-tubular channel.

7. The device of claim 1, wherein the microhotplate comprises silicon, polysilicon, silicon carbide, silicon nitride, or metal.

8. The device of claim 1, wherein the microcalorimeter further comprises a reference microhotplate, comprising a resistive heating element disposed on a side of the reference microhotplate and an electrical control circuit for powering the resistive heating element and monitoring the change in the electrical characteristics of the resistive heating element, to correct the active microhotplate signal for non-combustion variations in the signal caused by the fuel sample flowing over the heated microhotplates.

9. The device of claim 1, wherein the catalyst comprises a noble metal, noble metal with additives, semiconducting oxide, or hexaluminate material.

10. The device of claim 9, wherein the catalyst further comprises a support.

11. The device of claim 10, wherein the support comprises alumina, hexaaluminate, zirconia, ceria, titania, hydrous metal oxide, or silica-doped hydrous zirconium oxide.

12. The device of claim 8, wherein the reference microhotplate does not comprise the catalyst.

13. The device of claim 8, wherein the reference microhotplate comprises a support.

14. The device of claim 13, wherein the support comprises alumina, hexaaluminate, zirconia, ceria, titania, hydrous metal oxide, or silica-doped hydrous zirconium oxide.

\* \* \* \* \*